United States Patent [19]

Sharvit et al.

[11] Patent Number: 5,091,578
[45] Date of Patent: Feb. 25, 1992

[54] METHOD OF PREPARING PHENOXY ETHERS FOR USE AS AGROCHEMICAL INTERMEDIATES

[75] Inventors: Joseph Sharvit, Lehavim; Abraham A. Pereferkovich, Kfar Sava; Daniel Shohat, Beer Sheva, all of Israel

[73] Assignee: Makhteshim Chemical Works Ltd., Beer Sheva, Israel

[21] Appl. No.: 537,968

[22] Filed: Jun. 14, 1990

[30] Foreign Application Priority Data

Jun. 21, 1989 [IL] Israel .......................... 90702
May 10, 1990 [IL] Israel .......................... 94355

[51] Int. Cl.$^5$ .................. C07C 213/02; C07C 217/30
[52] U.S. Cl. ................................. 564/399; 564/354; 564/353; 568/630; 568/655; 568/656
[58] Field of Search .............. 564/399, 354, 353; 514/651; 568/629, 630, 655, 656, 776, 774

[56] References Cited

FOREIGN PATENT DOCUMENTS 243038 10/1987 European Pat. Off. .
0296673 12/1988 European Pat. Off. .
1469772 4/1977 United Kingdom .

*Primary Examiner*—Glennon H. Hollrah
*Assistant Examiner*—Shailendra Kumar
*Attorney, Agent, or Firm*—Browdy and Neimark

[57] ABSTRACT

N-n-propyl-N-2-(2,4,6-trichlorophenoxy)-ethylamine is prepared by selectively chlorinating 2-phenoxy ethanol by reacting it with chlorine either in the presence of hydrogen chloride at a temperature of from −10° C. to 50° C. or in the presence of urea at a temperature of from 20° C. to 55° C. in a water/carbon tetrachloride solvent mixture to form 2-(2,4,6-trichlorophenoxy)ethanol; reacting the 2-(2,4,6-trichlorophenoxy)ethanol with thionyl chloride in the presence of a catalytic amount of tetraalkyl ammonium chloride, optionally in the presence of a solvent to form 2-(2,4,6-trichlorophenoxy)ethyl chloride; and reacting the 2-(2,4,6-trichlorophenoxy) ethyl chloride with n-propylamine at a temperature of from 20° C. to 150° C., optionally in the presence of water to form N-n-propyl-N-2-(2,4,6-trichlorophenoxy) ethyl amine.

22 Claims, No Drawings

METHOD OF PREPARING PHENOXY ETHERS FOR USE AS AGROCHEMICAL INTERMEDIATES

BACKGROUND OF THE INVENTION

The present invention concerns the improved process for preparing 2-(2,4,6-trichlorophenoxy)-ethyl chloride and N-n-propyl-N-2-(2,4,6-trichlorophenoxy)ethyl amine and their use in the manufacture of Prochloraz.

2-(2,4,6-Trichlorophenoxy)-ethyl chloride and N-n-propyl-N-2-(2,4,6-trichlorophenoxy)-ethyl amine are used as intermediates in preparing the fungicide Prochloraz.

According to GB 1,469,772, the classical method of preparing Prochloraz begins with 2,4,6-trichlorophenol. This process suffers from several disadvantages. First of all, the trichlorophenol must be in a highly pure form to avoid the formation of tarry by-products in the subsequent steps of preparing Prochloraz. Second, the processes used to purify 2,4,6-trichlorophenol most often lead to the formation of undesireable chlorinated by-products. Furthermore, the use of 2,4,6-trichlorophenol to prepare Prochloraz requires the reaction of the former under basic conditions, which can also lead to the formation of similar chlorinated by-products.

Recent reports have tried to avoid the problems. Thus, EP 243,038 describes a process of preparing 2,4,6-trichlorophenol involving the slowcontrolled chlorination of phenol in the presence of a catalyst which is alleged to diminish the formation of the chlorinated by-products. EP 299,892 describes the chlorination of a chlorophenol using a different type of catalyst.

Nevertheless, even if the formation of unwanted chlorinated by-products are avoided, the standard process for preparing Prochloraz according to GB 1,469,772 involves the need to handle 2,4,6-trichlorophenol and ethylene dibromide—themselves both highly toxic and carcinogenic materials.

OBJECTIVES OF THE INVENTION

It is the objective of the present invention to provide a new and improved method for the preparation of 2-(2,4,6-trichlorophenoxy) ethyl chloride and N-n-propyl-N-2-(2,4,6-trichlorophenoxy)-ethyl amine. It is a further objective of the present invention to provide a method for the preparation of these compounds without having to handle the highly toxic and carcinogenic 2,4,6-trichlorophenol and ethylene dibromide. A further objective is the provision of a method for the preparation of these compounds in high yields substantially free of the chlorinated by-product.

SUMMARY OF THE INVENTION

It has unexpectedly been discovered that N-n-propyl-N-2-(2,4,6-trichlorophenoxy)-ethyl amine may be prepared comprising the steps of:

1. Selectively chlorinating 2-phenoxy-ethanol by reacting it with chlorine
    (a) in the presence of hydrogen chloride at a temperature of from $-10°$ C. to $50°$ C.; or
    (b) in the presence of urea at a temperature of from $20°$ C. to $55°$ C. in a water/carbon tetrachloride solvent mixture, to form 2-(2,4,6-trichlorophenoxy)-ethanol.

2. Reacting the 2-(2,4,6-trichlorophenoxy)-ethanol with thionyl chloride in the presence of a catalytic amount of a tetra-alkyl ammonium halide at a temp. of from $30°$ C. to $100°$ C., optionally in the presence of a solvent to form 2-(2,4,6-trichlorophenoxy)-ethyl chloride;

3. Reacting the 2-(2,4,6-trichlorophenoxy)-ethyl chloride with n-propyl amine at a temperature of from $20°$ C. to $150°$ C., optionally in the presence of water, to form N-n-propyl-N-2-(2,4,6-trichlorophenoxy)-ethyl amin; and 4. Recovering the N-n-propyl-N-2-(2,4,6-trichlorophenoxy)-ethyl amine formed.

DETAILED DESCRIPTION OF THE INVENTION

The reaction process is generally illustrated below, on a batch-wise basis:

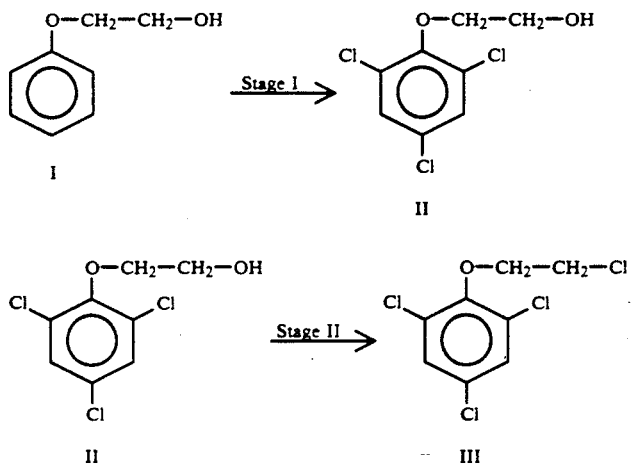

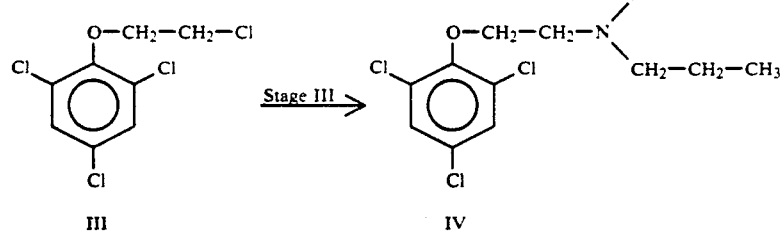

In carrying out the process of Stage I(a) of the present invention, chlorine is reacted with 2-phenoxyethanol at a temperature of from −10° C. to 50° C. in the presence of hydrogen chloride. The most suitable rate at which the chlorine gas is fed will vary with the reaction temperature. This stage can only be carried out by reacting at least three moles of chlorine per mole of 2-phenoxy-ethanol. In practice, an excess of chlorine is used.

It was unexpectedly found that the ether alcohol, 2-phenoxyethanol, can be selectively chlorinated, in the presence of hydrogen chloride since ether alcohols are usually very easily hydrolysed by hydrogen chloride. The initial concentration of hydrogen chloride may vary from 5% to 32%. However, the lower the initial concentration of hydrogen chloride is, the lower the yields. It is, therefore, preferred to use higher initial concentrations of hydrogen chloride; with an initial concentration of 32% most preferred.

While a temperature range for Stage I(a) of −10° C. to 50° C. was sufficient for the reaction to proceed, the lower and higher ends of this range afforded lower yields. A preferred temperature range was 0° C. to 25° C.

In carrying out the process of Stage I(b) of the present invention, chlorine is reacted with 2-phenoxyethanol at a temperature of from 20° C. to 55° C. in the presence of urea. The most suitable rate at which the chlorine gas is fed will vary with the reaction temperature. This stage can only be carried out by reacting at least three moles of chlorine per mole of 2-phenoxy-ethanol. In practice, an excess of 20 percent of chlorine is used.

A small amount of urea was found to markedly improve the yield of the reaction and the purity of the product of Stage I(b). The ratio of urea to 2-phenoxyethanol which was found to improve the reaction is 1:4 to 1:70, preferably 1:10 to 1:20 and most preferably 1:14, by weight.

Running Stage I(b) without water afforded black polymeric material. If this stage is not run in the presence of carbon tetrachloride, the selectivity of the chlorination is greatly effected. The reaction is, therefore, preferably run in the presence of a mixed water/carbon tetrachloride solvent, in a ratio of 1:1 to 1:50, preferably 1:10 by volume, respectively.

While the processes of either Stage I(a) or Stage I(b) can be used, the process of Stage I(a) is preferred. The reasons are that the process of Stage I(a) affords higher yields and higher selectivity resulting in a purer final product and avoiding the use of carbon tetrachloride as solvent.

The temperature of reaction of Stage II may range from 30° C. to 100° C. At the lower end of the temperature range the reaction is not economical. At the higher end of the temperature range the reaction is difficult to control. The preferred temperature range is from about 50° C. to 80° C.

Stage II may be run either with or without the use of a solvent. A suitable solvent is one inert to thionyl chloride; example being toluene, xylene, halogenated hydrocarbons such as chloroform, dichloro-ethane and carbon tetra-chloride. Halogenated hydrocarbons are preferred, with carbon tetrachloride being the most preferred. In addition, the use of a catalyst such as a tetra-alkyl ammonium halide, was found necessary for this stage. The alkyl group of the tetra-alkyl ammonium halide may be chosen from the group consisting of straight or branched alkyl groups having from 1 to 16 carbon atoms, such as methyl, ethyl, propyl, butyl, pentyl, heptyl, decyl and the like, cyclic alkyl groups such as cyclopentyl, cyclohexyl, cycloheptyl, cyclodecyl and the like and benzyl. Preferred alkyl groups are straight chain alkyl groups having from 1 to 8 carbon atoms and benzyl. Most preferred are methyl and benzyl, with the preferred halide as chloride. An especially preferred catalyst is benzyl trimethyl ammonium chloride.

The temperatures of reaction of Stage III may range from 20° C. to 150° C. At the lower end of the temperature range the reaction is too slow to be economical. At the higher end of the temperature range lower yields are obtained due to polymerization and decomposition. The preferred temperature range is from about 75° C. to 90° C.

Stage III may be either run neat or in the presence of water. It is preferred from a chemical point of view to run the reaction in water, for then a lower temperature (75° C. instead of 90° C.) and lower pressure (1.7 to 2.3 atmospheres instead of 2.2 to 3 atmospheres) can be used. However, for technical reasons, it is sometimes preferred to run this stage without water.

The final amine product can be isolated as a mineral acid salt, preferably as the hydrochloride acid addition salt, which forms nice white crysals which are easily handled. However, if necessary, the free amine may be isolated by treating the hydrochloride salt with a base such as, for example, aqueous sodium carbonate to neutralize to pH 7, separate the phases and distill the organic layer to yield an oil boiling at 112°-114° C./0.2 mm Hg.

Thus the present invention affords a process for preparing 2-(2,4,6-trichlorophenoxy)-ethyl chloride and N-n-propyl-N-2-(2,4,6-trichlorophenoxy)ethyl amine in high yield, without having to handle the highly toxic and carcinogenic 2,4,6-trichlrophenol and ethylene dibromide. In addition, the latter amine product may be reacted with phosgene and subsequently with imidazole according to GB 1,469,772 to afford Prochloraz, having essentially no detectable amount of the undesireable chlorinated by-products.

While the invention will now be described in connection with certain preferred embodiments in the following examples, it will be understood that it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

EXAMPLE 1

Preparation of 2-(2,4,6-trichlorophenoxy)-ethanol: in the presence of hydrogen chloride (Stage I (a))

Into a three-necked, round-bottomed 1-liter flask fitted with a stirrer, thermometer, reflux condenser, and a gas sparger are added 70 g of 2-phenoxyethanol dissolved in 125 ml of HCl (32%). The reaction mixture is cooled with stirring to 0°–25° C. and chlorine gas is added at a rate sufficient to keep the temperature at 0° C. 5° C. cooling when necessary. During the reaction a second liquid phase appears. After adding two thirds of the chlorine (about 7 hours) the temperature is raised to 25° C. and the remaining chlorine is added at a slower rate (additional 8 hours) where a total of 125 g of chlorine are added. The stirring is stopped and the lower organic layer is poured into 100 ml of 20% stirred solution of sodium bisulfite kept at a temperature of 70° C. A 10% sodium hydroxide solution is added until a pH of 7.5 is reached, the stirring is stopped, the lower organic layer is separated, dissolved in 150 ml methanol and 50 ml water kept at 45° C. The resulting solution is cooled to 0°–5° C. to precipitate the crystalline product. The crystals are filtered, washed with water, and dried to yield 2-(2,4,6-trichlorophenoxy)-ethanol in a yield of 88% having a purity of 98–99%.

EXAMPLE 2

Preparation of 2-(2,4,6-trichlorophenoxy)-ethanol in the presence of urea (Stage I(b))

Into a three-necked, round-bottomed 1-liter flask fitted with a stirrer, a dip-pipe to convey gas, a thermometer and a reflux condenser, 140 g 2-phenoxy ethanol, 250 ml carbon tetrachloride, 25 ml water and 10 g urea were introduced. Chlorine gas was then added while stirring and keeping the temperature at 20° C. via cooling. When the temperature reached about 55° C. the rate of chlorine addition was lowered so that the cooling kept the temp. at 55° C. in spite of the exotherm. Chlorine gas was added until the solution became yellow. The rate of chlorine addition was further lowered until the yellow color disappeared. At this stage it became necessary to heat the reaction mixture to keep the temperature at 55° C. The end of the reaction was determined by GLC. Addition of chlorine was stopped and the mixture washed with NaHSO$_3$(10%) and then with water. The mixture was then washed with a bicarbonate solution until a pH of 8 was reached and then with additional water. Cooling the organic phase to 5° C. with a gentle stirring caused the precipitation of white crystals to afford 135 g of 2-(2,4,6-trichlorophenoxy)-ethanol at a concentration of 96%. The mother liquor was recycled as solvent for subsequent batches of chlorination, purging about 15%. The overall yield after several runs of chlorination reaches 80%.

EXAMPLE 3

Preparation of 2-(2,4,6-trichlorophenoxy)-ethyl chloride

Into a three-necked, round-bottom flask fitted with a stirrer, thermometer, reflux condenser and dropping funnel was added 250 g of 96% 2-(2,4,6-trichlorophenoxy) ethanol, 250 ml carbon tetrachloride and 4 g of benzyl-trimethyl-ammonium chloride. The mixture was heated to 55° C. and 146 g thionyl chloride was added dropwise over 1.5 hours. After the addition of the thionyl chloride the temperature of the reaction was slowly raised to 80° C. for a total reaction tme of 2.5 to 3 hours. The end of the reaction was determined by GLC. The mixture was cooled to 60° C. and water slowly added to decompose the excess thionyl chloride. The phases were separated and the organic phase was washed with a 10% sodium hydroxide solution until it reached a pH of 7. After an additional separation of the phases the organic phase was washed again with water. After a further separation of phases, the carbon tetrachloride was distilled off to yield an oil which slowly crystallized to form 257 g of 2-(2,4,6-trichlorophenoxy)-ethyl chloride in a purity of 96%–98% and yield of 98%.

EXAMPLE 4

Following the method of Example 3, the reaction was run without carbon tetrachloride as solvent. The only differences are as follows:

The thionyl chloride was added dropwise to a melted 2-(2,4,6-trichlorophenoxy)-ethanol at a temperature of 70° C. After addition of about 10% of the thionyl chloride, the temperature was lowered to 50° C. and the reaction continued as before. At the end of the reaction, when the final separation of the organic layer was done, there was no need to distill off any solvent, affording a similar yield and purity.

EXAMPLE 5

Preparation of N-n-propyl-N-2-(2,4,6-trichlorophenoxy) ethyl amine

Into a 1-liter glass reactor, which could withstand a pressure of 6 atmospheres, fitted with a stirrer, heating mantle and a pressure gauge, were added 270.8 g 2-(2,4,6-trichlorophenoxy) ethyl chloride and 350 g n-propyl amine. The mixture was slowly heated with stirring over a period of 8 hours at a temperature of 90° C. The initial pressure under these conditions was 3 atmospheres, which dropped during the reaction to about 2.2 atmospheres. The end of the reaction was determined by GLC. At the end of the reaction the mixture was cooled to 55° C., whereupon the pressure dropped to atmospheric. The excess n-propyl amine was distilled off and it could be recycled for use in a subsequent batch, until a bottom temperature of 85° C. was reached. At the end of the distillation the mixture was cooled to 40° C., 300 ml of a 20% hydrogen chloride solution and 1 g of an emulgator GAF RM-510 were added. The temperature rose to 70° C., the mixture was stirred for one hour at this temperature and the product precipitated as white crystals of the amine hydrochloride salt. The slurry is cooled to 40° C., filtered, re-slurried in 250 ml xylene and filtered again. This affords 312 g of white hydrochloride salt of N-n-propyl-N-2-(2,4,6-trichlorophenoxy)-ethyl amine in 93% yield and purity of 96%-98%.

EXAMPLE 6

Following the method of Example 4, the same reaction was run in the presence of 60 g water. The only differences were that the maximum temperature was only 75° C., with a total reaction time of only 5 hours; the initial pressure was 2.3 atmospheres and the final pressure 1.7 to 1.8 atmospheres. This afforded N-n-propyl-N-2-(2,4,6-trichlorophenoxy)-ethyl amine of similar yield and purity.

We claim:

1. A process for preparing N-n-propyl-N-2-(2,4,6-trichlorophenoxy)-ethyl amine of the formula:

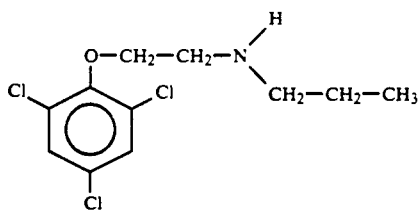

characterized in that:

a. 2-phenoxy ethanol of the formula

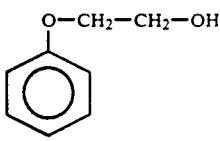

is selectively chlorinated by reaction with chlorine (1) in the presence of hydrogen chloride at a temperature of from −10° C. to 50° C.; or (2) in the presence of urea at temperature of from 20° C. to 55° C. in a water/carbon tetrachloride solvent to form 2-(2,4,6-trichlorophenoxy)-ethanol of the formula;

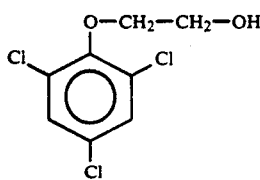

b. the 2-(2,4,6-trichlorophenoxy)-ethanol is reacted with thionyl chloride in the presence of a catalytic amount of tetra-alkyl ammonium halide having from 1 to 16 carbon atoms or benzyl trimethyl ammonium halide at a temperature of 30° C. to 100° C., optionally in the presence of a solvent, to form 2-(2,4,6-trichlorophenoxy)-ethyl chloride of the formula:

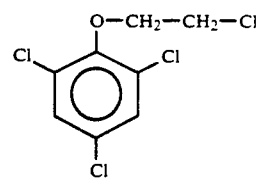

c. the 2-(2,4,6-trichlorophenoxy)-ethyl chloride is reacted with n-propyl amine at a temperature of from 20° C. to 150° C., optionally in the presence of water, to form N-n-propyl-N-2-(2,4,6-trichlorophenoxy)-ethyl amine; and d. the N-n-propyl-N-2-(2,4,6-trichlorophenoxy)-ethyl amine formed is recovered.

2. A process in accordance with claim 1 wherein the concentration of hydrogen chloride in Stage I ranges from 5% to 32%.

3. A process in accordance with claim 1 wherein the initial concentration of hydrogen chloride in Stage I(a) ranges from 20% to 32%.

4. A process in accordance with claim 1 wherein Stage I(a) is run at a temperature range of from 0° C. to 25° C.

5. A process in accordance with claim 1 wherein the ratio of urea to 2-phenoxy-ethanol in Stage I(b) ranges from 1:4 to 1:70 by weight.

6. A process in accordance with claim 1 wherein the the ratio of urea to 2-phenoxy-ethanol in Stage I(b) is 1:4 by weight.

7. A process in accordance with claim 1 wherein the ratio of water to carbon tetrachloride in Stage I(b) ranges from 1:1 to 1:50 by volume.

8. A process in accordance with claim 1 wherein the ratio of water to carbon tetrachloride in Stage I(b) is 1:10 by volume.

9. A process in accordance with claim 1 wherein the solvent of Stage II is chosen from the group consisting of toluene, xylene and chlorinated hydrocarbons.

10. A process in accordance with claim 1 wherein the solvent of Stage II is chosen from the group consisting of chloroform, dichloromethane, dichloroethane and carbon tetrachloride.

11. A process in accordance with claim 1 wherein the solvent of Stage II is carbon tetrachloride.

12. A process in accordance with claim 1 wherein the tetra-alkyl ammonium halide in Stage II is tetra-alkyl ammonium chloride.

13. A process in accordance with claim 1 wherein the alkyl group of the tetra-alkyl ammonium halide in Stage II is chosen from the group consisting of straight chain alkyl groups having from 1 to 6 carbon atoms.

14. A process in accordance with claim 1 wherein the ammonium halide in Stage II is benzyl-trimethyl-ammonium chloride.

15. A process in accordance with claim 1 wherein the ratio of tetra-alkyl-ammonium halide to 2-(2,4,6-trichlorophenoxy)-alcohol in Stage II is 1 to 250 by weight.

16. A process in accordance with claim 1 wherein the temperature of Stage II ranges from 50° C. to 80° C.

17. A process in accordance with claim 1 wherein Stage III is run in the presence of water.

18. A process in accordance with claim 1 wherein the temperature of Stage III ranges from 75° C. to 90° C.

19. A process for preparing N-n-propyl-N-2-(2,4,6-trichlorophenoxy)-ethyl amine characterized in that:

a. 2-phenoxy-ethanol is selectively chlorinated by the reaction of chlorine in the presence of 20% to 32% hydrogen chloride at a temperature of 0° C. to 25° C. to form 2-(2,4,6-trichlorophenoxy)-ethanol;

b. reacting the 2-(2,4,6-thrichlorophenoxy)-ethanol with thionyl chloride in the presence of benzyl-trimethyl-ammonium chloride in a ratio of 1:60 by weight, at a temperature of from 50° C. to 80° C., in the presence of carbon tetrachloride as solvent to form 2-(2,4,6-trichlorophenoxy)-ethyl chloride.

c. reacting the 2-(2,4,6-trichlorophenoxy)-ethyl chloride with n-propyl-amine in the presence of water at temperature of from 75° C. to 90° C. to form N-n-propyl-N-2-(2,4,6-trichlorophenoxy)-ethyl amine; and d. recovering the N-n-propyl-N-2-(2,4,6-trichlorophenoxy)-ethyl amine formed.

20. A process for preparing 2-(2,4,6-trichlorophenoxy)-ethyl chloride characterized in that:

a. 2-phenoxy ethanol is selectively chlorinated by the reaction of chlorine in the presence of 20% to 32% hydrogen chloride at a temperature of 0° C. to 25° C. to form 2-(2,4,6-trichlorophenoxy)-ethanol;

b. reacting the 2-(2,4,6-trichlorophenoxy)-ethanol with thionyl chloride in the presence of benzyl-trimethyl ammonium chloride in a ration of 1:60 by weight at a temperature of from 50° C. to 80° C., in the presence of carbon tetrachloride as solvent to form 2-(2,4,6-trichlorophenoxy)-ethyl chloride; and c. recovering the 2-(2,4,6-trichlorophenoxy)-ethyl chloride formed.

21. A process for preparing N-n-propyl-N-2-(2,4,6-trichlorophenoxy)-ethyl amine characterized in that:

a. 2-phenoxy-ethanol is selectively chlorinated by the reaction of chlorine in the presence of urea in a ratio of urea to 2-phenoxy-ethanol of 1 to 14 by weight at a temperature of 20° C. to 55° C. in a water/carbon tetrachloride solvent in a ratio of water tocarbon tetrachloride of 1 to 10 by volume to form 2-(2,4,6-trichlorophenoxy)-ethanol;

b. reacting the 2-(2,4,6-trichlorophenoxy)-ethanol with thionyl chloride in the presence of benzyl-trimethyl-ammonium chloride in a ratio of 1:60 by weight, at a temperature of from 50° C. to 80° C., in the presence of carbon tetrachloride as solvent to form 2-(2,4,6-trichlorophenoxy)-ethyl chloride.

c. reacting the 2-(2,4,6-trichlorophenoxy)-ethyl chloride with n-propyl-amine in the presence of water at temperature of from 75° C. to 90° C. to form N-n-propyl-N-2-(2,4,6-trichlorophenoxy)-ethyl amine; and d. recovering the N-n-propyl-N-2-(2,4,6,trichlorophenoxy)-ethyl amine formed.

22. A process for preparing 2-(2,4,6-trichlorophenoxy)-ethyl chloride characterized in that:

a. 2-phenoxy ethanol is selectively chlorinated by the reaction of chlorine in the presence of urea in a ratio of urea to 2-phnoxy-ethanol of 1 to 14 by weight at a temperature of 20° C. to 55° C. in a water/carbon tetrachloride solvent in a ratio of water to carbon tetrachloride of 1 to 10 by volume to form 2-(2,4,6-trichlorophenoxy)-ethanol;

b. reacting the 2-(2,4,6-trichlorophenoxy)-ethanol with thionyl chloride in the presence of benzyl-trimethyl ammonium chloride in a ratio of 1:60 by weight at a temperature of from 50° C. to 80° C. in the presence of carbon tetrachloride as solvent to form 2-(2,4,6-trichlorophenoxy)-ethyl chloride; and c. recovering the 2-(2,4,6-trichlorophenoxy)-ethyl chloride formed.

* * * * *